US010113968B2

United States Patent
Tang et al.

(10) Patent No.: US 10,113,968 B2
(45) Date of Patent: Oct. 30, 2018

(54) SPECIFIC DETECTION AND QUANTIFICATION OF CARDIOLIPIN AND ISOLATED MITOCHONDRIA BY POSITIVELY CHARGED AIE FLUOROGENS AND METHOD OF MANUFACTURING THEREOF

(71) Applicant: The Hong Kong University of Science and Technology, Hong Kong (CN)

(72) Inventors: Benzhong Tang, Hong Kong (CN); Yuning Hong, Hong Kong (CN); Wai Tung Leung, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 95 days.

(21) Appl. No.: 15/100,707

(22) PCT Filed: Dec. 3, 2014

(86) PCT No.: PCT/CN2014/092898
§ 371 (c)(1),
(2) Date: Jun. 1, 2016

(87) PCT Pub. No.: WO2015/081860
PCT Pub. Date: Jun. 11, 2015

(65) Prior Publication Data
US 2016/0299078 A1    Oct. 13, 2016

Related U.S. Application Data

(60) Provisional application No. 61/963,393, filed on Dec. 3, 2013.

(51) Int. Cl.
*G01N 21/64*    (2006.01)
*G01N 33/483*    (2006.01)

(52) U.S. Cl.
CPC ..... *G01N 21/6458* (2013.01); *G01N 21/6428* (2013.01); *G01N 33/483* (2013.01)

(58) Field of Classification Search
None
See application file for complete search history.

(56) References Cited

U.S. PATENT DOCUMENTS

2003/0110840 A1*  6/2003  Arriaga ............. G01N 15/1404
                                                                 73/61.72
2012/0172296 A1     7/2012  Tang et al.

FOREIGN PATENT DOCUMENTS

| CN | 101243321 A | 8/2008 |
| CN | 101679849 A | 3/2010 |
| CN | 102702096 A | 10/2012 |
| WO | 2013029340 A1 | 3/2013 |

OTHER PUBLICATIONS

Hong et al., Aggregation-Induced Emission: phenomenon, mechanism and applications, The Royal Society of Chemistry, Chemical Communications, p. 4332-4353, 2009.*
Petit et al., 10N-Nonyl acridine orange interacts with cardiolipin and allows the quantification of this phospholipid in isolated mitochondria, European Journal of Biochemistry, vol. 209, pp. 267-273, 1992.*
Fernandez et al., Use of the Xuorescent dye 10-N-nonyl acridine orange in quantitative and location assays of cardiolipin: a study on diVerent experimental models, Analytical Biochemistry 328 (2004) 174-180, (Year: 2004).*
International Search Report dated Jan. 23, 2015 corresponding to International application No. PCT/CN2014/092898.

* cited by examiner

*Primary Examiner* — Taeyoon Kim
*Assistant Examiner* — Srikanth Patury
(74) *Attorney, Agent, or Firm* — Nath, Goldberg & Meyer; Joshua B. Goldberg; Nahied Usman

(57) ABSTRACT

The present subject matter relates to a one-step method of detecting and quantifying cardiolipin in a sample using a positively charged AIE luminogen by introducing the AIE luminogen to a solution containing the sample and measuring fluorescence intensity of the solution; a method of quantifying isolated mitochondria using a positively charged AIE luminogen by staining a sample containing isolated mitochondria with the AIE luminogen and measuring the fluorescence intensity; and a method of quantifying isolated mitochondria using a positively charged AIE luminogen by introducing the AIE luminogen to a sample containing isolated mitochondria, wherein the AIE luminogen stains the isolated mitochondria and identifying the stained isolated mitochondria under microscope. With improved sensitivity and excellent selectivity to CL over other major mitochondrial membrane lipids, an aggregation-induced emission-active fluorogen, TTAPE-Me, may serve as a valuable fluorescent sensor for CL detection and quantification and the quantification of isolated mitochondria.

6 Claims, 10 Drawing Sheets

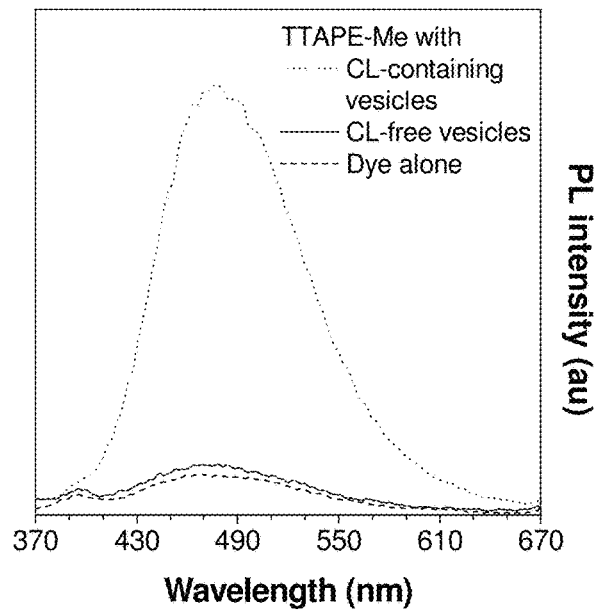
FIG. 1
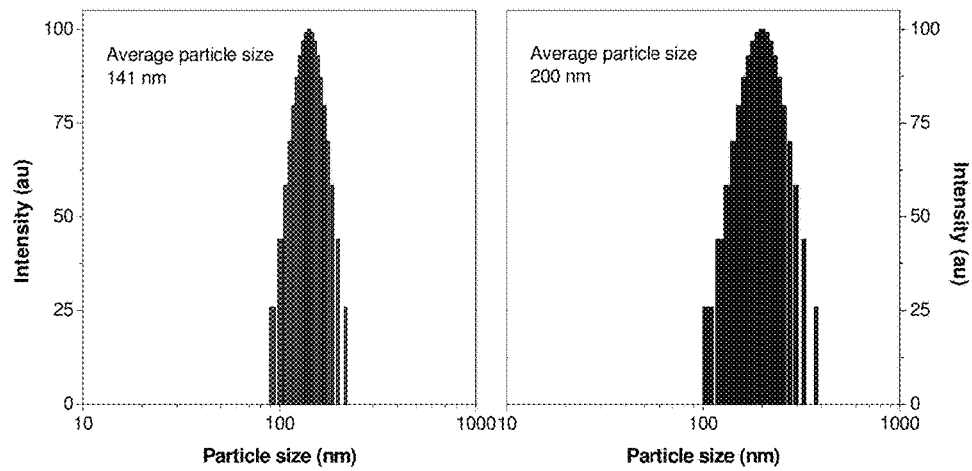
FIG. 2A    FIG. 2B

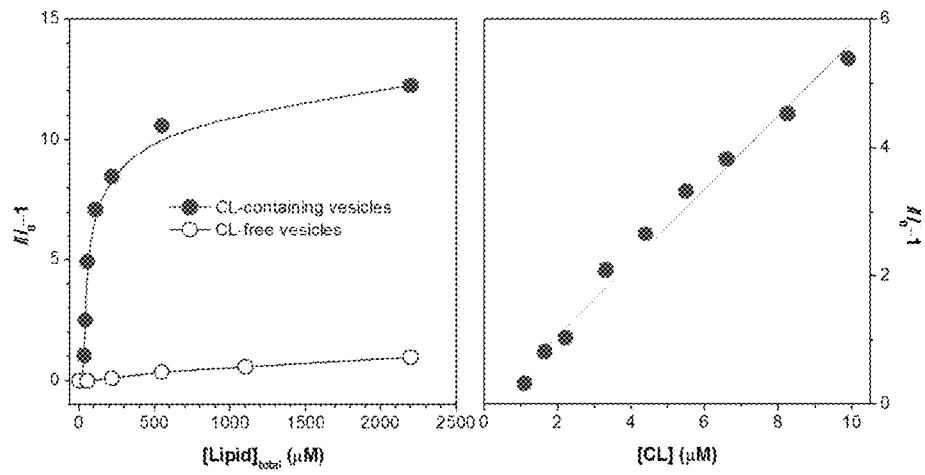
FIG. 3A    FIG. 3B
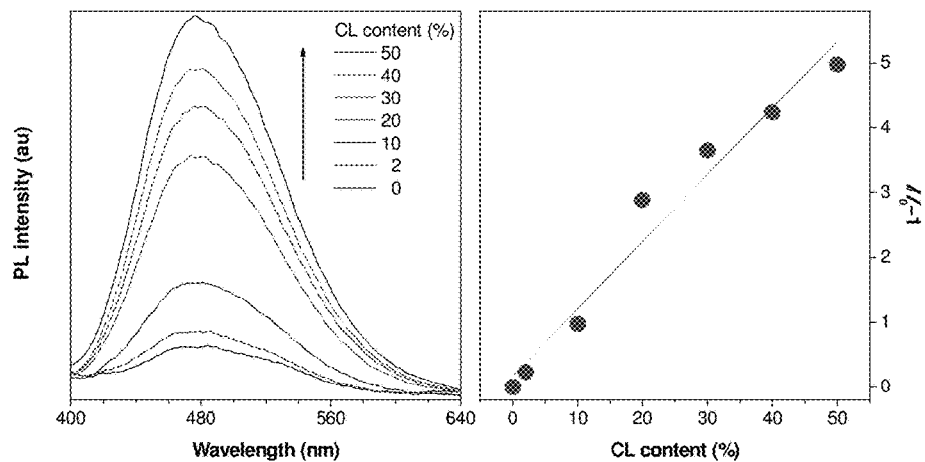
FIG. 4A    FIG. 4B

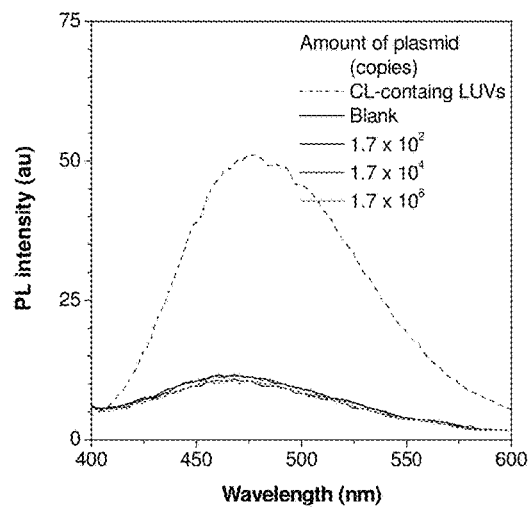
FIG. 8
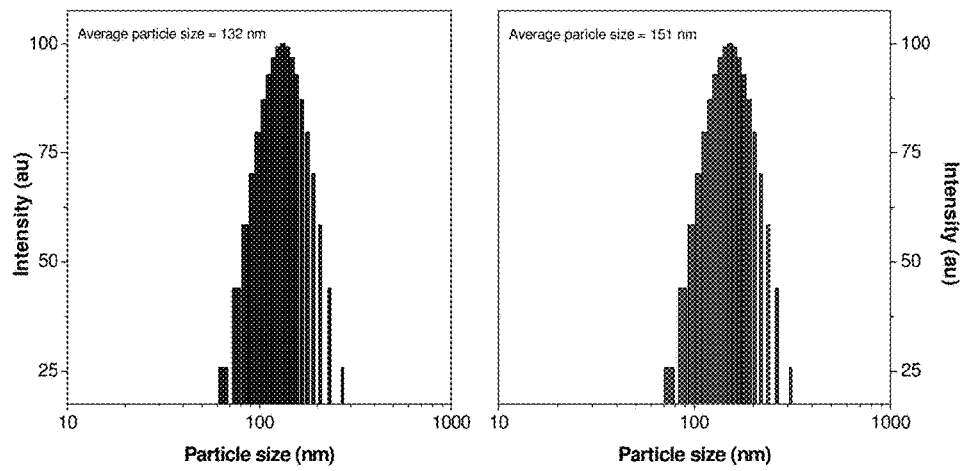
FIG. 9A  FIG. 9B

SPECIFIC DETECTION AND QUANTIFICATION OF CARDIOLIPIN AND ISOLATED MITOCHONDRIA BY POSITIVELY CHARGED AIE FLUOROGENS AND METHOD OF MANUFACTURING THEREOF

RELATED APPLICATIONS

The present patent application claims priority to provisional U.S. Patent Application No. 61/963,393 filed Dec. 3, 2013, which was filed by the inventors hereof and is incorporated by reference herein in its entirety.

TECHNICAL FIELD

The present subject matter relates to a compound or salt which can quantify cardiolipin (CL) specifically, as well as quantify and identify isolated mitochondria, particularly from *Saccharomyces cerevisiae* (*S. cerevisiae*) strain YPH 500 of yeast.

BACKGROUND

Eukaryotic cells use approximately 5% of their genes to synthesize lipids. Such a heavy portion is invested because of the indispensable functions of lipids in cells. With their unique structures, lipids form bilayers to segregate the internal constituents from the extracellular environment as well as to compartmentalize discrete organelles. In addition to their barrier function, lipids are also used for energy storage in lipid droplets and as messengers in signal transduction and molecular recognition processes.

Cardiolipin is a diphosphatidylglycerol lipid exclusively found in the mitochondrial inner membrane. CL regulates enzymatic activities involved in electron transport and oxidative phosphorylation. This unique lipid consists of four unsaturated acyl chains and a polar head with two negative charges, having the structure:

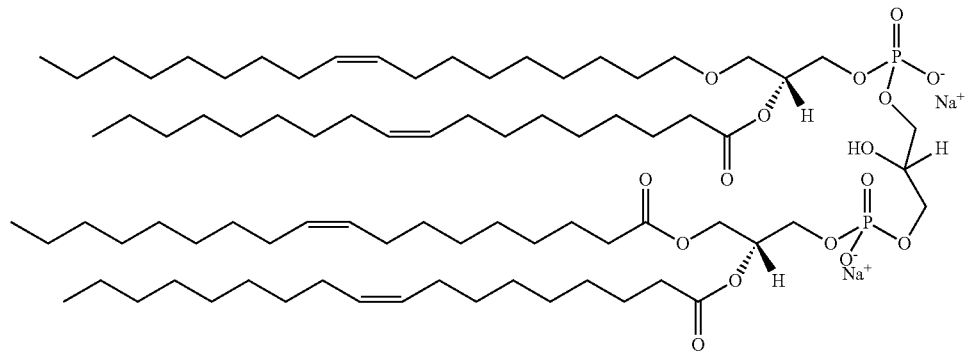

Tetraoleoyl cardiolipin (TOCL)

Interaction of CL with the protein cytochrome c (cyt c) activates the peroxidase activity of the protein and triggers mitochondria-mediated apoptosis. During apoptosis, the distribution of CL changes, which consequently affects ATP synthesis in mitochondria. Meanwhile, the level of CL decreases during apoptosis in a time-dependent manner, correlating with the release of cyt c to the cytosol (intracellular fluid or cytoplasmic matrix found inside cells) and the generation of reactive oxygen species.

In addition to having an important role in the apoptosis pathway, the CL level of mitochondria is also of clinical significance. The depletion of CL is a critical indicator of aging and Barth syndrome, as well as a number of diseases associated with mitochondrial respiratory function including heart ischemia, reperfusion, gliomas, cardiac hypertrophy, and cardiac failure. Tangier disease is caused by the abnormal enhanced production of CL. Parkinson's disease, HIV-1, and various cancers are reported to be associated with the abnormalities of CL. Therefore, developing effective methods for detection and quantification of CL is of high importance.

Prior art examples of various methods for quantifying cardiolipin include those disclosed by William Kenneth Lang (US 2004/0096903 A1), Wonhwa Cho (US 2012/0225447 A1), Ruey-min Lee (US 2006/0172958 A1), Fatih M. Uckun (US 2001/0044442 A1), and Robert E. Davis (US 2001/0021526 A1). However, these prior art examples generally face several problems, such as lacking a standard protocol, involving extra substrates, and involving sophisticated methods.

Particularly, specific detection of CL among numerous phospholipids is not trivial. Lipidomics profiling by high-resolution liquid chromatograph mass spectrometry (LC-MS) has recently been developed for quantitative analysis of CL. This powerful method requires sophisticated instrumentation and experienced operators, which limit the scope of its application.

Optical detection by fluorescence, on the other hand, is a relatively simple and accessible method while providing superior sensitivity. In the early 1980s, a fluorescent dye, 10-N-nonyl acridine orange (NAO) was introduced for CL detection and mitochondria staining, NAO having the structure:

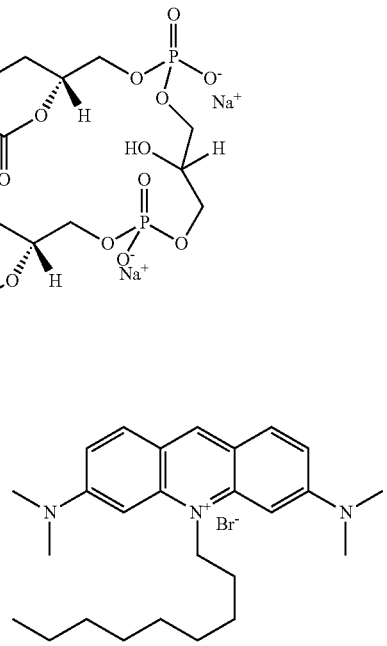

Nonyl acridine orange (NAO)

The green fluorescence of NAO is decreased in the presence of CL. However, the quantification of CL by NAO is not realistic, as both the excitation and emission maxima are dependent on the dye concentration, and the linear relationship can be established only when the NAO/CL molar ratio is equal to 2. To quantify mitochondria with NAO, tortuous steps are involved, including mitochondria fixation, long time incubation, and centrifugation. Furthermore, NAO suffers from small Stokes shift and poor water-solubility, making NAO less appealing for use in biological systems. The working mechanism of NAO is still unclear and the performance is difficult to improve, even through different approaches. Although there are numerous drawbacks, NAO has been used for many years, even without a standard protocol, because no alternative has been developed so far.

SUMMARY

In search of alternatives, luminogens with aggregation-induced emission (AIE) characteristics have attracted attention. As opposed to conventional dyes, AIE luminogens are non-emissive when molecularly dissolved, but become highly fluorescent in the aggregate state, due to the restriction of intramolecular motions.

In one exemplary embodiment, the present subject matter describes a one-step method of detecting and quantifying cardiolipin in a sample using a positively charged AIE luminogen comprising introducing the AIE luminogen to a solution containing the sample and measuring fluorescence intensity of the solution.

In another exemplary embodiment, the present subject matter describes a method of quantifying isolated mitochondria using a positively charged AIE luminogen comprising staining a sample containing isolated mitochondria with the AIE luminogen and measuring the fluorescence intensity.

In a third exemplary embodiment, the present subject matter describes a method of quantifying isolated mitochondria using a positively charged AIE luminogen comprising introducing the AIE luminogen to a sample containing isolated mitochondria, wherein the AIE luminogen stains the isolated mitochondria and identifying the stained isolated mitochondria under a microscope.

BRIEF DESCRIPTION OF THE DRAWINGS

FIG. 1 shows emission spectra of TTAPE-Me in the absence and presence of vesicles, with and without CL. CL-containing vesicles are composed of TOCL/DOPC (1:1 molar ratio), and CL-free vesicles are composed of pure DOPC, respectively, in a 25 mM HEPES buffer at pH 7.4. [dye]=10 μM; [lipid]$_{total}$=22 μM; $\lambda_{ex}$=350 nm.

FIG. 2A is a particle analysis of CL-containing vesicles. CL-containing vesicles are composed of TOCL/DOPC (1:1 molar ratio) in a 25 mM HEPES buffer at pH 7.4. Total lipid concentration: 22 μM.

FIG. 2B is a particle analysis of CL-free vesicles. CL-free vesicles are composed of pure DOPC in a 25 mM HEPES buffer at pH 7.4. Total lipid concentration: 22 μM.

FIG. 3A is a plot of the fluorescence enhancement (I/I$_0$−1) of TTAPE-Me at 480 nm with CL-containing and CL-free vesicles.

FIG. 3B is the linear region of the I/I$_0$−1 value versus CL concentration. [dye]=10 μM; $\lambda_{ex}$=350 nm.

FIG. 4A shows the emission spectra of TTAPE-Me in the presence of LUVs with different CL content (2-50% TOCL).

FIG. 4B is a plot of the fluorescence enhancement at 480 nm versus CL content. [dye]=10 μM; [lipid]$_{total}$=22 μM; $\lambda_{ex}$=350 nm.

FIG. 8 shows the emission spectra of TTAPE-Me in the presence of different amounts of DNA (pUC 18 DNA, 2686 bp). (TTAPE-Me with CL-containing LUVs is shown for comparison) [dye]=10 μM; $\lambda_{ex}$=350 nm.

FIG. 9A shows particle analysis of the all-component LUVs with TOCL (17% TOCL, 39.5% DOPC, 38.8% DPPE, 1.7% Soy PI, 1% DOPS & 2% SM) in a 25 mM HEPES buffer at pH 7.4.

FIG. 9B shows particle analysis of the all-component LUVs without TOCL (56.5% DOPC, 38.8% DPPE, 1.7% Soy PI, 1% DOPS & 2% SM) in a 25 mM HEPES buffer at pH 7.4.

DETAILED DESCRIPTION

Figure 5:
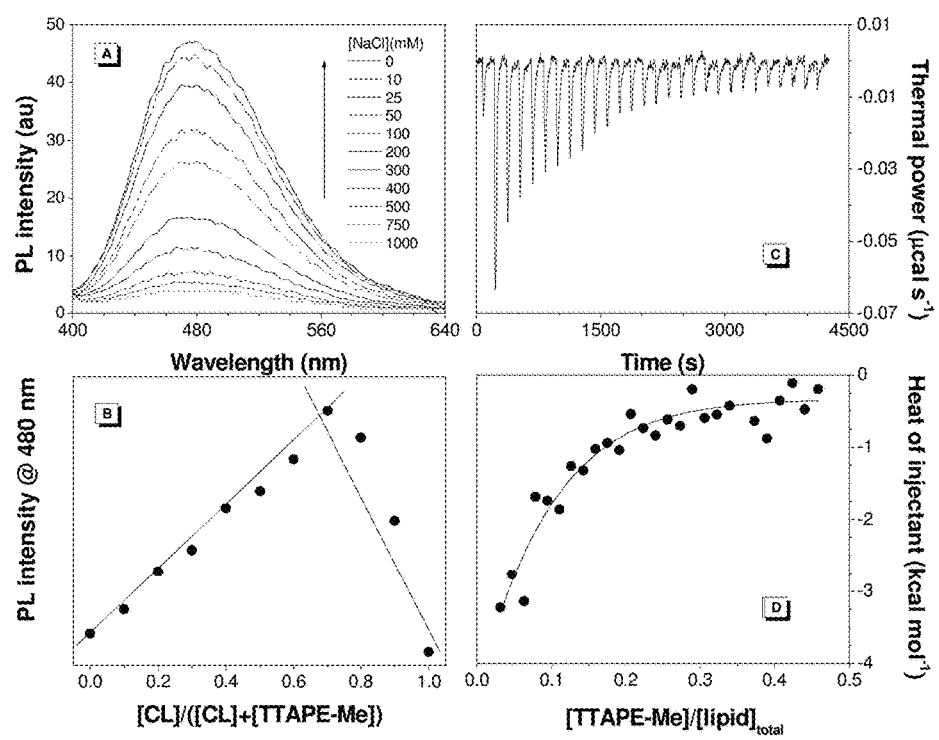
FIG. 5 shows (A) Emission spectra of TTAPE-Me with CL-containing vesicles in the presence of varying concentrations of NaCl. [dye]=10 μM; [lipid]$_{total}$=22 μM; λex=350 nm. (B) Job plot for determination of the binding stoichiometry of TTAPE-Me to CL-containing vesicles. The total concentration of TTAPE-Me and CL is kept at 20 μM. (C) calorimetric curves for titration of CL-containing vesicles with serial injections of TTAPE-Me at 25° C. (D) Binding isotherm as a function of [TTAPE-Me]/[lipid]$_{total}$ molar ratio. CL-containing vesicles are composed of TOCL and DOPC (1:1 molar ratio).

The inventors have discovered that certain AIE luminogens may be used to quantify CL and isolated mitochondria.

More specifically, these AIE luminogens may be administered to a sample, cell, or vesicle, whereby the cell is imaged. The CL or isolated mitochondria may then be quantified.

The AIE luminogen may be fluorogen TTAPE-Me. The TTAPE-Me may be linked to a lipid binding protein, which may be a lipid binding fragment of any protein.

The CL may be cytosolic or in a membrane. The membrane may be a cellular membrane or in the form of a lipid vesicle. The lipid vesicle may be a large unilamellar vesicle (LUV), whereby the diameter of the vesicle is between about 60 nm and 800 nm, 70 nm and 800 nm, 80 nm and 800 nm, 90 nm and 800 nm, 100 nm and 700 nm, 200 nm and 600 nm, 300 nm and 500 nm, 400 nm and 800 nm, 500 nm and 800 nm, 600 nm and 800 nm, or 700 nm and 800 nm.

The cellular membrane may be a eukaryote cell membrane. The eukaryote cell membrane may be mammalian, wherein the mammalian cell membrane may be a structural component of an epithelial cell, a fibroblast, a keratinocyte, a macrophage, a monocyte, a muscle cell, or a nerve cell.

Provided herein is a method of quantifying CL or isolated mitochondria. The AIE luminogen may be administered or introduced to a biological sample, a cell, or lipid vesicle, wherein the AIE luminogen binds to CL or isolated mitochondria. The AIE luminogen-bound CL or AIE luminogen-bound isolated mitochondria complex may then be quantified based upon image analysis of the cell or lipid vesicle.

Definitions

Unless defined otherwise, all technical and scientific terms used herein have the same meanings as commonly understood by someone ordinarily skilled in the art to which the present subject matter pertains. The following definitions are provided for the purpose of understanding the present subject matter and for constructing the appended patent claims.

The phrase "aggregation induced emission" or "AIE" as used herein refers to the phenomenon manifested by compounds exhibiting enhancement of light-emission upon aggregation in the amorphous or crystalline (solid) states whereas they exhibit weak or almost no emission in dilute solutions.

The phrase "emission intensity" as used herein refers to the magnitude of fluorescence/phosphorescence normally obtained from a fluorescence spectrometer or a fluorescence microscopy measurement.

The term "luminogen" as used herein refers to a chemical compound that manifests luminescence.

The term "fluorogen" as used herein refers to a chemical compound that manifests luminescence.

The term "fragment" as used herein refers to a portion of a reference peptide, polypeptide, or nucleic acid sequence.

The term "isolating" or "isolated" as used herein refers to a process for separating mitochondria from a mitochondria containing material where at least one undesired component or contaminant with which it is normally associated is contained. The term "isolating" includes "separating," "purifying" and/or "clarifying." No particular level of isolation of mitochondria is required.

The term "aryl" refers to an aromatic carboxcyclic group having a single ring, for example a phenyl ring; multiple rings, for example biphenyl; or multiple condensed rings in which at least one ring is aromatic, for example naphthyl, 1,2,3,4-tetrahydronaphthyl, anthryl, or phenanthryl, which can be unsubstituted or substituted with one or more other substituents as defined above.

The term "heteroaryl" as used herein refers to a heterocycle in which at least one ring is aromatic. A heterocycle is a saturated, unsaturated, or aromatic carbocyclic group having a sing ring, multiple rings, or multiple condensed rings, and having at least one hetero atom such as nitrogen, oxygen, or sulfur within at least one of the rings.

The term "alkyl" as used herein refers to a branched or unbranched hydrocarbon chain comprising a designated number of carbon atoms. For example, $C_1$-$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like. It is also contemplated as with the scope of the present subject matter that "alkyl" may also refer to a hydrocarbon chain wherein any of the carbon atoms of the alkyl are optionally replaced with O, NH, S, or $SO_2$. For example, carbon 2 of n-pentyl can be replaced with O to form propyloxymethyl.

The phrase "unsaturated alkyl" as used herein refers to a branched or unbranched unsaturated hydrocarbon chain comprising a designated number of carbon atoms. For example, a $C_2$-$C_6$ straight or branched alkenyl hydrocarbon chain contains 2 to 6 carbon atoms having at least one double bond, and includes but is not limited to substituents such as ethenyl, propenyl, iso-propenyl, butenyl, iso-butenyl, tert-butenyl, n-pentenyl, n-hexenyl, and the like. It is also contemplated as within the scope of the present subject matter that "unsaturated alkyl" may also refer to an unsaturated hydrocarbon chain wherein any of the carbon atoms of said unsaturated alkyl are optionally replaced with O, NH, S, or $SO_2$. For example, carbon 2 of 4-pentene can be replaced with O to form (2-propene)oxymethyl.

The term "cycloalkyl" as used herein refers to an organic cyclic substituent comprising a designated number of carbon atoms. For example, a $C_3$-$C_8$ cycloalkyl contains three to eight carbon atoms forming a three, four, five, six, seven, or eight-membered ring, including, for example, a cyclopropyl, cyclobutyl, cyclopentyl, cyclohexyl, cycloheptyl, or cyclooctyl ring, and the like.

The term "a" or "an" as used herein includes the singular and the plural, unless specifically stated otherwise. Therefore, the term "a," "an," or "at least one" can be used interchangeably in this application.

Throughout the application, descriptions of various embodiments use "comprising" language. However, it will be understood by one of skill in the art that in some specific instances an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

List of Abbreviations Used

AIE aggregation-induced emission
bp base pair
BSPOTPE water-soluble AIE luminogen
CL cardiolipin
cyt c cytochrome c
DOPC (1,2-dioleoyl-sn-glycero-4-phosphocholine)
DOPS (1,2-dioleoyl-sn-glycero-3-phospho-L-serine (sodium salt))
DPPE (1,2-dipalmitoleoyl-sn-glycero-3-phosphoethanolamine)
HEPES 4-(2-hydroxyethyl)-1-piperazineethanesulfonic acid
$I/I_0$ fluorescence enhancement
ITC isothermal titration calorimetry
LC-MS liquid chromatograph mass spectrometer
$\lambda_{em}$ emission maximum
$\lambda_{ex}$ excitation wavelength
LUV large unilamellar vesicle
M molar
MHz megahertz
mL milliliter
mM millimolar
mmol millimole
mtDNA mitochondrial DNA
NAO 10-N-nonyl acridine orange
nm nanometer
NMR nuclear magnetic resonance
ppm part per million
pUC plasmid cloning vector
*S. cerevisiae* Saccharomyces cerevisiae
SEM scanning electron microscopy
SM N-hexanoyl-D-sphingomyelin
soy PI L-α-phosphatidylinositol (Soy) (sodium salt)
TOCL 1,1',2,2'-tetraoleoyl cardiolipin
TPE tetraphenylethene
TTAPE-Me 1,1,2,2-tetrakis[4-(2-trimethylammonioethoxy)phenyl]ethene tetrabromide
UV ultra violet
μm micrometer Administration The AIE luminogen may be administered or introduced to a biological sample, cell or lipid vesicle. The AIE luminogen may be injected into the sample, cell, or vesicle. The AIE luminogen may be transfected into the sample, cell, or vesicle via a protein transfection agent. The transfection agent may be an Influx® pinocytic cell-loading agent or a lipid formulation, such as a BIOPORTER® transfection agent.

The sample may comprise one or more cells and/or one or more lipid vesicles. The cell or lipid vesicle may be derived from any cell type, tissue, or bodily fluid from a subject and may include sections of tissues such as biopsy and autopsy samples, frozen sections taken for histologic purposes, blood, hair, mucus, plasma, saliva, serum, skin, sputum, stool, and tears. Cell types and tissues may also include ascetic fluid, cerebrospinal fluid, gynecological fluid, lung tissue or cells, lymph fluid, peritoneal fluid, urine, a fluid collected by vaginal rinsing, or a fluid collected by vaginal flushing. A tissue or cell type may be provided by removing a sample of cells from a subject, but may also be accomplished by using previously isolated cells, such as cells isolated by another person, at another time, and/or for another purpose. Archival tissues may also be used, such as those having treatment or outcome history.

Imaging

The AIE luminogen-containing cell or lipid vesicle may be subjected to image analysis. Image analysis may involve the use of an imaging microscopy system, particularly fluorescence microscopy, confocal microscopy, and/or two-photon microscopy.

Quantification

The CL in a cell or lipid vesicle may be quantified via ratiometric analysis or calculation based on sFCS (scanning fluorescence correlation spectroscopy). With respect to ratiometric analysis, a calibration curve may be provided. The curve may be based on $F_B/F_G$ versus the target lipid, wherein the F values are determined by photon counting, in corresponding different band pass filter channels, of imaged lipid vesicles or cells containing FLBP (fluorescent lipid binding protein) and having a known concentration of the target lipid and, optionally, one or more other lipids. The calibration curve may then be used to determine the concentration of the target lipid.

For cell and/or cell membrane measurements, minimum $F_B$ values may be taken from the cytosol and maximum $F_B$ values assessed after an excess amount of the target lipid is administered to the cell. Cellular CL concentration may then be determined from the observed $F_B/F_G$ values using the calibration curve described above.

Disorders

The method of quantifying CL and isolated mitochondria may be used to diagnose a disorder and/or a cancer. A comparison of the quantified CL or isolated mitochondria to a reference standard may indicate whether a lipid metabolizing enzyme is functioning properly. The reference standard may be the quantity present in a comparable sample from an individual with or without the disorder.

The disorder may include depletion of CL, diseases associated with mitochondrial respiratory function, abnormal enhanced production of CL, and abnormalities of CL. Particularly, the disorder may include aging, Barth syndrome, heart ischemia, reperfusion, gliomas, cardiac hypertrophy, cardiac failure, Tangier disease, Parkinson's disease, HIV-1, and various cancers.

Kits/Assays

The present subject matter provides an assay method which involves the step of detecting and/or measuring the binding of an AIE luminogen when the AIE luminogen is exposed to a protein in a test sample. Such an assay may involve the steps of identifying and/or isolating said protein by binding to said AIE luminogen. Said AIE luminogen may be used to detect/measure/identify and/or isolate more than one type of cardiolipin binding protein from a test sample containing many proteins. More than one type of AIE luminogen may be used to detect/measure/identify and/or isolate more than one type of cardiolipin binding protein. The test sample may be a tissue or tissue culture extract, preferably a lysed extract. The test sample may be obtained by lysis of cells in a buffer containing at least one non-ionic surfactant, such as 1RITON® X-100 or NP-40. The AIE luminogen may be exposed to said test sample in the presence or absence of soluble cardiolipin. Protein-probe binding may be compared between more than one test sample to determine cardiolipin binding protein variation between said samples.

Detergent may be used in assays of the present subject matter to reduce non-specific binding to the AIE luminogen. Where the AIE luminogen comprises a cardiolipin derivative covalently attached to beads or other microparticles, detergent may be used to enhance the solubility of the beads/microparticles.

Further, an AIE luminogen coupled to scintillant may be used to identify an agonist or antagonist of the interaction of a cardiolipin binding protein with cardiolipin. Such uses are particularly suited for high throughput screening of candidate agonists/antagonists, especially single step high throughput screening. A radio labelled protein (radio labelled for example with tritiated leucine, or 35S-methionine) known to bind cardiolipin is tested for binding to a probe of the invention coupled to scintillant in the presence and absence of one or more candidate agonists and/or antagonists. The advantage of using an AIE luminogen coupled to a scintillant is that the difference in signal obtained between normal binding (i.e. in a control sample without any candidate antagonist or agonist) of cardiolipin binding protein to the AIE luminogen and reduced or enhanced binding (i.e. in samples with agonist or antagonist) is much greater than can be obtained without the scintillant. Consequently, agonists and antagonists can be more readily identified.

A general approach for identifying cardiolipin binding proteins from tissue extracts is as follows: The tissue is homogenized using standard methods, and two fractions are produced, cytosol and membranes. The cytosol fraction is mixed 1:1 with buffer A (50 mM Tris-HCl pH 8.0, 150 mM NaCl, 10 mM EDTA, 1% NP-40, protease inhibitors) and then incubated with a probe of the invention equilibrated for 30 min in buffer B (50 mM Tris-HCl pH 7.5, 150 mM NaCl, 5 mM EDTA, 0.1% Tween-20, 0.02% Na azide). The membrane fraction is mixed 1:3 with buffer A containing 2% NP-40 for 30 minutes on ice. The sample is then spun at 100,000 Xg for one hour to produce a soluble membrane extract. This extract is mixed with cardiolipin beads (i.e. probes of the invention in which the solid phase is a bead) equilibrated as described above and processed similarly as above. The sample is put in a rotator at 4 C for 2 hours, and then washed three times with buffer B in the cold. These washes are very important since they remove non-specifically bound proteins. The following modification provides an extra level of specificity: excess soluble cardiolipin is added to one of duplicate samples before the beads are introduced (the soluble cardiolipin solution is made by drying C:12 or C:8 cardiolipin dissolved in chloroform, resuspending in buffer A and sonicating for 5 minutes to make a stock solution of 250 mM). The assumption is that excess soluble cardiolipin will compete with the cardiolipin on the beads, thus reducing the amount of protein that is recovered bound to the beads. Bands of interest are excised from the gel and treated with trypsin. The tryptic digests produced from the various bands are analyzed by mass spectroscopy.

The AIE luminogens of the present subject matter can be used as general analytical tools for identification of cardiolipin binding proteins from different tissues and biological fluids. The cytosolic and membrane contents of any cell type likely can be screened for cardiolipin binding proteins using these AIE luminogens. In all cases, cytosolic or membrane fractions could be subjected to assays as described above.

The presently claimed subject matter has multiple aspects, illustrated by the following non-limiting examples.

In one exemplary embodiment, the present subject matter describes a one-step method of detecting and quantifying cardiolipin in a sample using a positively charged AIE luminogen comprising introducing the AIE luminogen to a solution containing the sample and measuring fluorescence intensity of the solution.

In another exemplary embodiment, the present subject matter describes a method of quantifying isolated mitochondria using a positively charged AIE luminogen comprising staining a sample containing isolated mitochondria with the AIE luminogen and measuring the fluorescence intensity.

In another exemplary embodiment, the present subject matter describes a method of quantifying isolated mitochondria using a positively charged AIE luminogen comprising introducing the AIE luminogen to a sample containing isolated mitochondria, wherein the AIE luminogen stains the isolated mitochondria and identifying the stained isolated mitochondria under microscope. In particular, the stained isolated mitochondria can be identified preferably under optical microscope, and more preferably under fluorescence microscope.

In an exemplary embodiment, the AIE luminogen used in any of the methods contemplated herein comprises a backbone structure having a formula selected from the group consisting of:

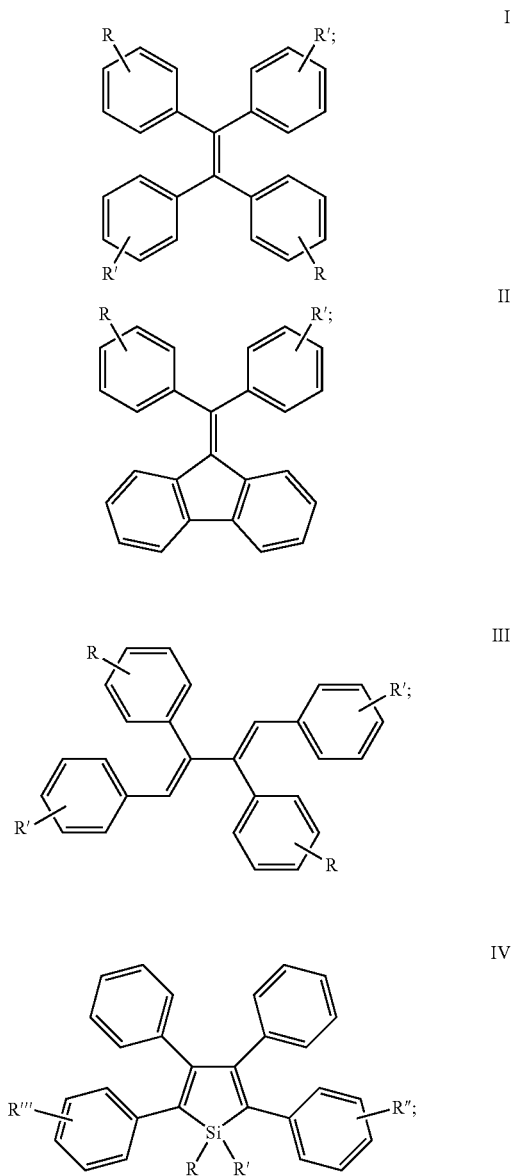

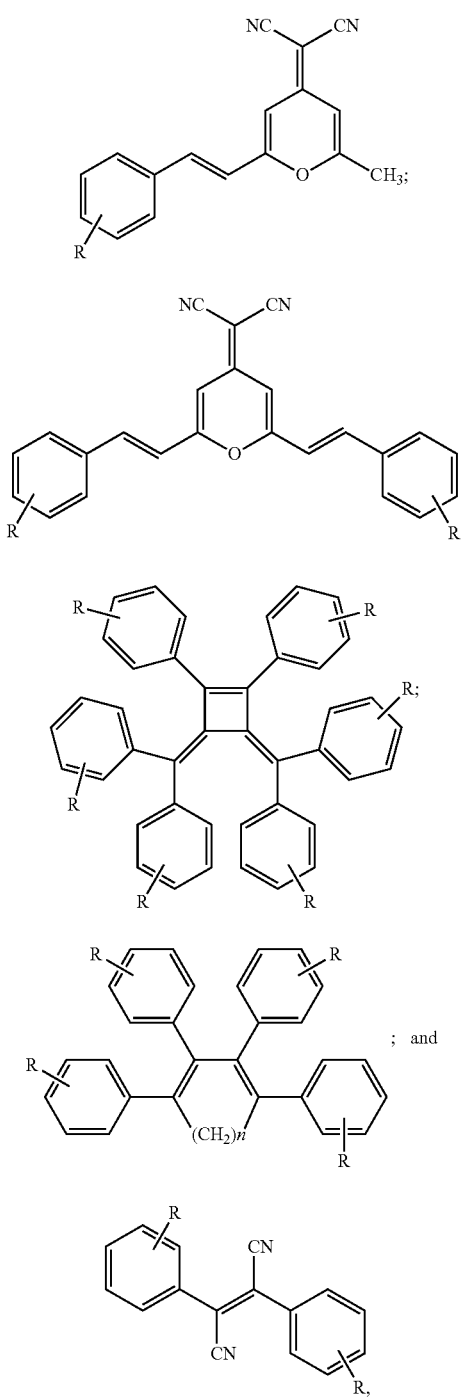

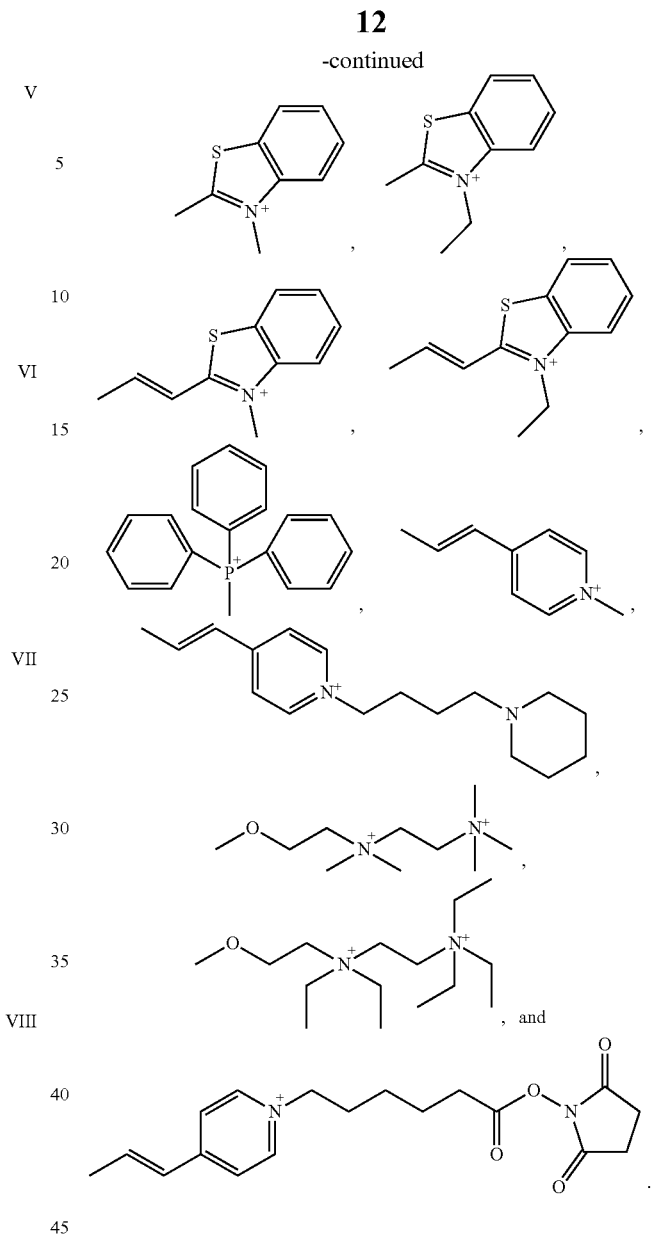

wherein each R, R', R" and R'" can independently be selected from

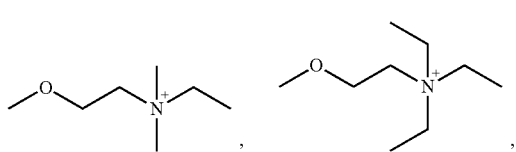

Compounds 1-4

Because it was proposed that specific cardiolipin probing by the AIE luminogen is based on electrostatic interaction between the probe and the target analyte, positively charged AIE luminogens were investigated for use. The AIE luminogens investigated for CL detection include Compounds 1-4 as follows:

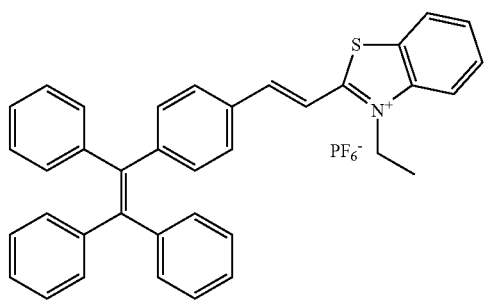

-continued

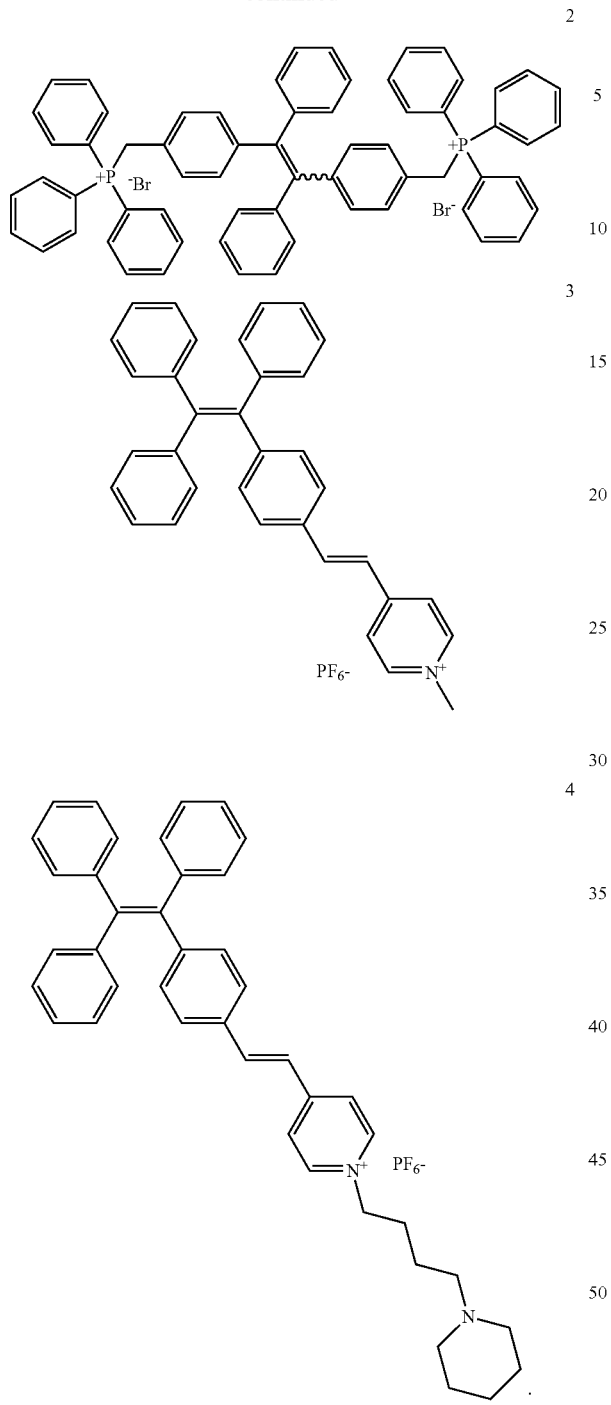

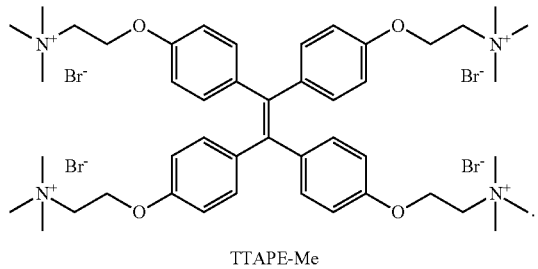

TTAPE-Me

The AIE fluorogen TTAPE-Me is synthesized as follows:

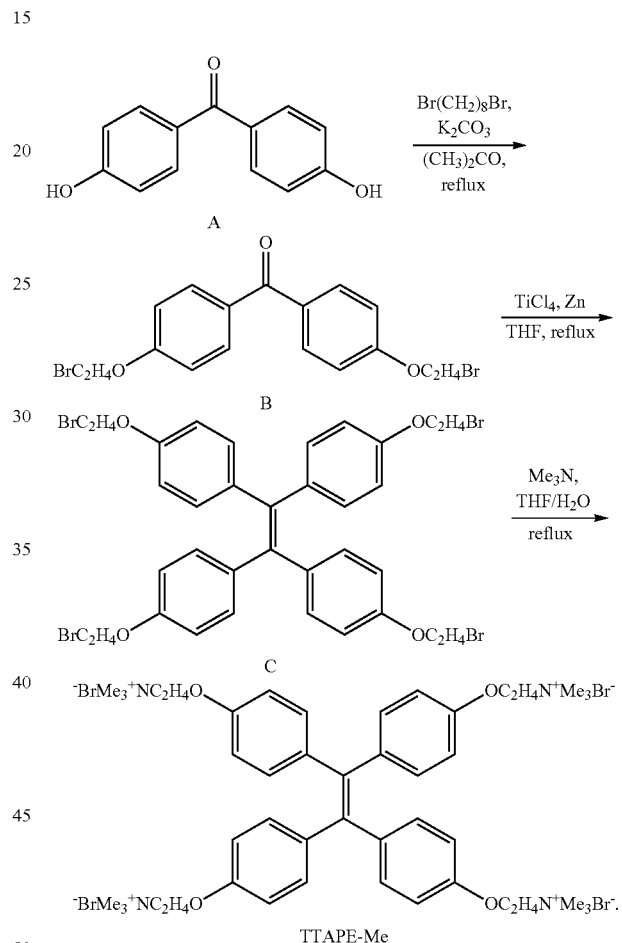

FIGS. 11-15 show the emission spectra of Compounds 1-4.

TTAPE-Me

I. CL Quantification

In an exemplary embodiment, inspired by the specific interaction of cyt c with CL, a positively charged AIE fluorogen has been designed and synthesized for CL detection. The AIE fluorogen designed is 1,1,2,2-tetrakis[4-(2-trimethylammonio-ethoxy)phenyl]ethene tetrabromide (TTAPE-Me) and has the following structure:

Based on the AIE mechanism, the TTAPE-Me dye should turn on fluorescence upon binding to CL-containing membranes, which may enable detection and quantification of CL. With the aid of its quaternary ammonium substituents, TTAPE-Me is completely soluble and thus non-fluorescent in aqueous solution, in accord with the general property of AIE luminogens. As shown in FIG. 1, the emission of TTAPE-Me is turned on in the presence of CL-containing vesicles.

The fluorescence of TTAPE-Me increases significantly upon the increase of the total lipid concentration of the CL-containing vesicles, while the emission of TTAPE-Me remains rather weak for the CL-free vesicles (FIG. 3A). The fluorescence enhancement ($I/I_0-1$) of TTAPE-Me at 480 nm is in a linear fashion in the CL concentration of 0-10 μM (FIG. 3B), which lies in the physiological range of CL in mitochondrial membrane. Linear detection of CL can also be obtained with the varying content of TOCL (2-50% TOCL) in the vesicles (FIG. 4A-4B). The results imply that flexible TTAPE-Me to CL ratio is allowed in the detection and quantification of CL. In contrast, conventional NAO requires strict 2:1 ratio of NAO/CL for quantitative measurement. Moreover, the detection of CL can be done immediately upon mixing the vesicles with the probe without any extra treatment.

TTAPE-Me is amphiphilic with the hydrophobic core of tetraphenylethene (TPE) and four quaternized ammonium moieties to promote its water affinity. As shown in FIG. 5A, ionic strength affects the fluorescence intensity of TTAPE-Me. With the increase of NaCl concentration, the fluorescence of the dye diminishes, which confirms that TTAPE-Me binds to CL via electrostatic attraction. The $Na^+$ ions compete with the bound dye molecules. Once the dye is released into solution, the intramolecular motions are no longer restricted and the fluorescence is turned off.

1,2-dioleoyl-sn-glycero-4-phosphocholine (DOPC) is the most abundant phospholipid in eukaryotic membranes and has the following structure:

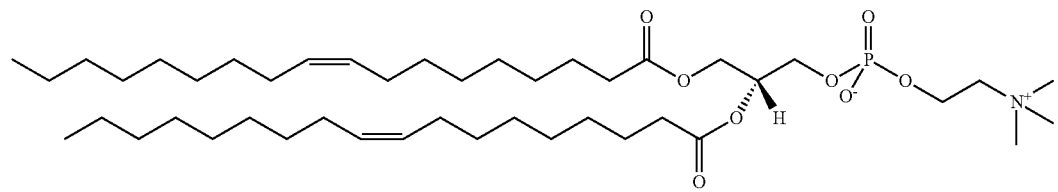

However, hydrophobic interaction is less likely to be involved. TTAPE-Me binds to CL only, though both CL and contain long alkyl chains.

BSPOTPE is a water-soluble AIE luminogen with two negative charges and has the following structure:

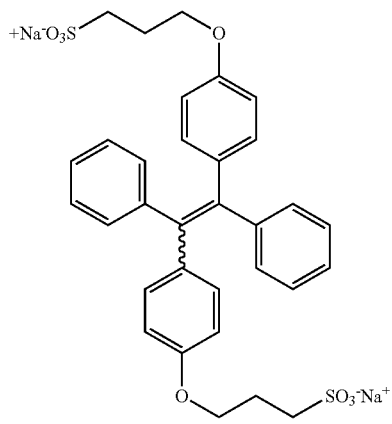

Figure 6:
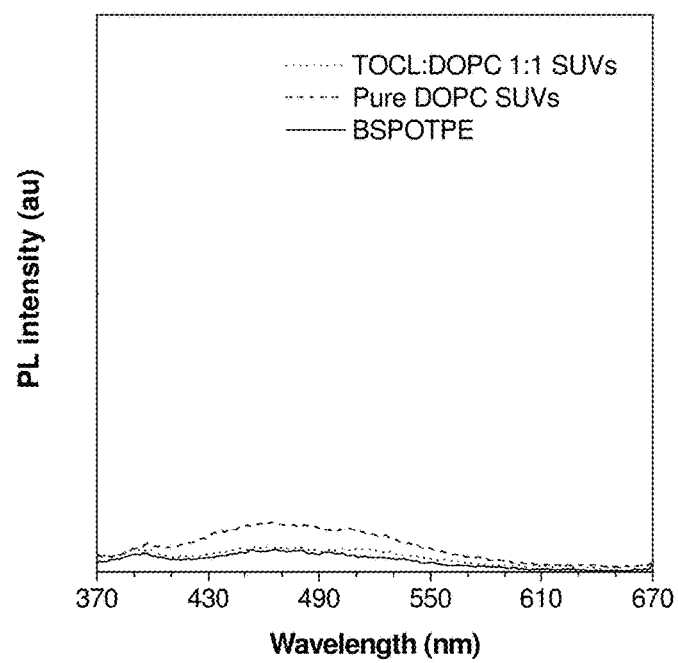
FIG. 6 shows emission spectra of BSPOTPE alone and with added CL-containing and CL-free vesicles. CL-containing and CL-free vesicles are composed of TOCL/DOPC (1:1 molar ratio) and pure DOPC, respectively, in a 25 mM HEPES buffer at pH 7.4. [dye]=10 μM; [lipid]$_{total}$=22 μM; $\lambda_{ex}$=350 nm.

BSPOTPE was used as a control because it exhibits no remarkable fluorescence enhancement with CL-containing vesicles (FIG. 6).

According to the AIE principle, TTAPE-Me is only fluorescent when bound, and thus the fluorescence can report the binding of TTAPE-Me to CL-containing vesicles. The emission intensity varying ratios of TTAPE-Me to CL-containing LUVs is then recorded and correlated to a Job plot (FIG. 5B). The plot has a peak at ~0.67, corresponding to a 2:1 binding ratio for TOCL to TTAPE-Me. The binding ratio perfectly matches the charge ratio, providing further support that the binding of TTAPE-Me towards CL is primarily driven by electrostatic interaction. Isothermal titration calorimetry (ITC) was employed to determine the affinity strength, which resulted in an indication that the interaction of TTAPE-Me to CL is an exothermic process (FIG. 5C). The binding curve was generated by integration of the area of each injection peak followed by the subtraction of the dilution heat of dye molecules (FIG. 5D). Fitting of the curve resulted in a dissociation constant of $2.08 \times 10^{-6}$ M.

To further evaluate the specificity of TTAPE-Me towards CL, the response of TTAPE-Me to other major lipids found on mitochondrial membranes was examined. The other major lipids evaluated were 1,2-dipalmitoleoyl-sn-glycero-3-phosphoethanolamine (DPPE):

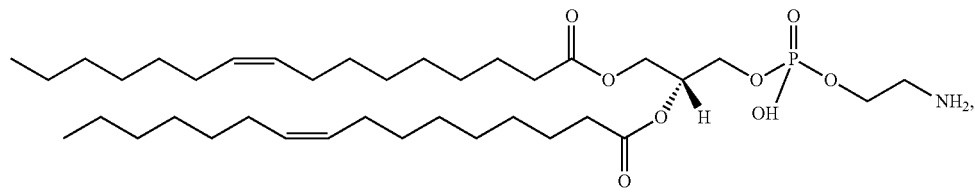 [SMILES: CCCCCC/C=C\CCCCCCCC(=O)OC[C@H](COP(=O)(O)OCCN)OC(=O)CCCCCCC/C=C\CCCCCC]

L-α-phosphatidylinositol (soy PI):

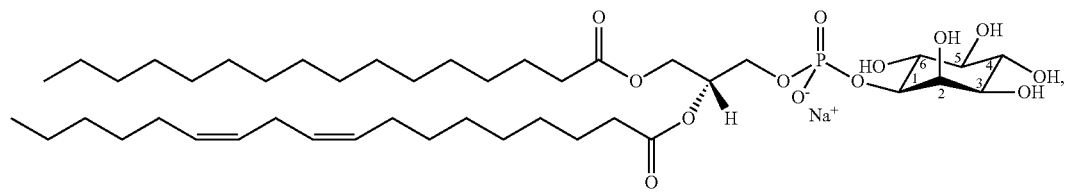

1,2-dioleoyl-sn-glycero-3-phospho-L-serine (DOPS):

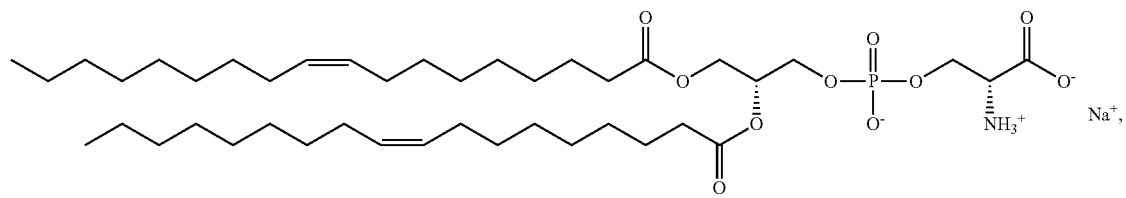 [SMILES: CCCCCCCC/C=C\CCCCCCCC(=O)OC[C@H](COP(=O)([O-])OC[C@@H]([NH3+])C(=O)[O-])OC(=O)CCCCCCC/C=C\CCCCCCCC]

and
N-hexanoyl-D-sphingomyelin (SM):

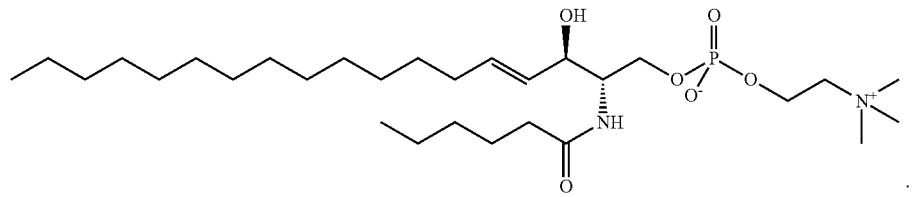 [SMILES: CCCCCCCCCCCCC/C=C/[C@@H](O)[C@H](COP(=O)([O-])OCC[N+](C)(C)C)NC(=O)CCCCC]

Six different types of LUVs were fabricated and were composed of each of the above lipids and TOCL and DOPC at the exact percentage as mitochondrial membrane, with the remaining percentage of each type of LUV filled by DOPC.

Figure 7:
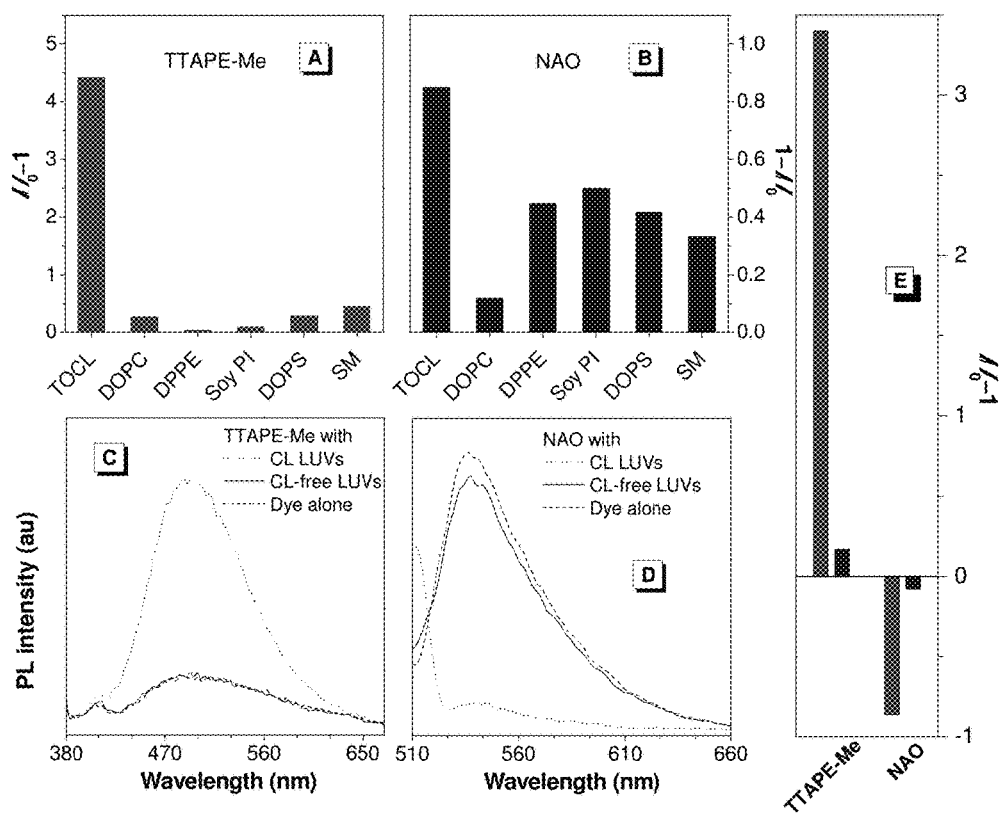
FIG. 7 shows change in fluorescence intensity of (A) TTAPE-Me and (B) NAO with vesicles of different lipid contents (left to right: 20% TOCL, 100% DOPC, 40% DPPE, 2% soy PI, 1% DOPS, and 2% SM; the remaining percentage of each type of vesicle is filled by DOPC). Emission spectra of (C) TTAPE-Me and (D) NAO with CL-containing and CL-free all-component vesicles are shown. (E) Bar chart of the change in fluorescence intensity shown in panels C and D (red: CL-containing vesicles, blue: CL-free vesicles). [dye]=10 μM; [lipid]$_{total}$=22 μM; for TTAPE-Me: $\lambda_{ex}$=350 nm and $\lambda_{em}$=480 nm; for NAO: $\lambda_{ex}$=499 nm and $\lambda_{em}$=530 nm.

As shown in FIG. 7A, the fluorescence of TTAPE-Me is selectively turned on with the TOCL vesicles, while other vesicles with the lipid components at the physiological concentrations do not cause any pronounced change of the fluorescence. While DOPS and PI are also negatively charged, they carry only one charge per molecule and share only 1% and 2% of the total mitochondrial membrane lipids, respectively (CL for ~20%). Hence, the presence of such small percentages of DOPS and soy PI do not affect the selectivity and sensitivity of TTAPE-Me for CL detection.

On the other hand, one might think that the negatively charged mitochondrial DNA (mtDNA) may interfere with the detection of CL by TTAPE-Me. However, in the control experiment, no fluorescence enhancement of TTAPE-Me in the presence of plasmids was observed. FIG. 8 shows plasmids, a model for the circular double-stranded mtDNA, at a wide range of concentrations, implying the presence of mtDNA would not complicate the CL quantification.

Meanwhile, to mimic the mitochondrial membranes, CL-containing and CL-free all-component LUVs were prepared. The CL-containing and CL-free all-component LUVs were composed by the mixture of all the above mentioned lipids at their physiological ratios (FIG. 9A-9B). With the CL-free all-component LUVs, the emission spectrum of TTAPE-Me remains identical to that of the free dye in buffer (FIG. 7C). With the CL-containing LUVs, the greenish-blue fluorescence is enhanced by over 3-fold (FIGS. 7C & E). Parallel experiments were conducted with NAO as the probe. NAO is a turn-off sensor whose fluorescence is decreased in the presence of CL (FIG. 7D). However, CL is not the only lipid that induces the decrease of NAO signals—other lipids such as DPPE, PI, or DOPS, can also induce the decrease of NAO signals to a large extent (FIG. 7B). In addition to the poor selectivity, the sensitivity of NAO is not comparable to that of TTAPE-Me (FIG. 7E).

II. Mitochondria Quantification

Figure 10A:
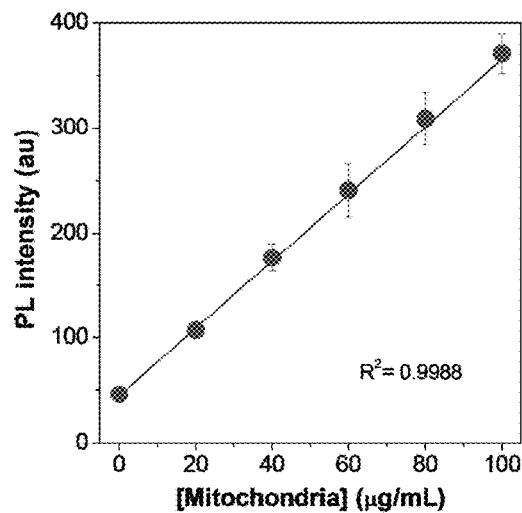
FIG. 10A shows emission intensity of TTAPE-Me at 480 nm with different amounts of yeast mitochondria in SEM buffer (250 mM sucrose, 1 mM EDTA, 10 mM MOPS-KOH, pH 7.2).
Figure 10B:
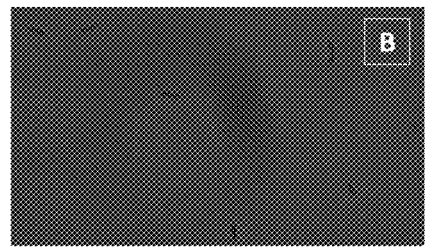
FIG. 10B shows an image of TTAPE-Me stained yeast mitochondria taken under daylight. [dye]=10 μM; $\lambda_{ex}$=350 nm.
Figure 10C:
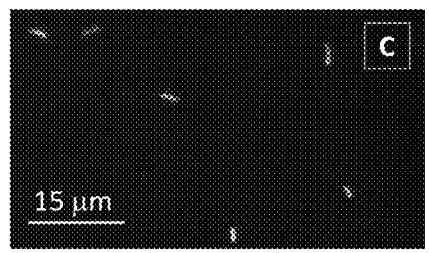
FIG. 10C shows an image of TTAPE-Me stained yeast mitochondria taken with UV illumination. [dye]=10 μM; $\lambda_{ex}$=350 nm.
Figure 11:
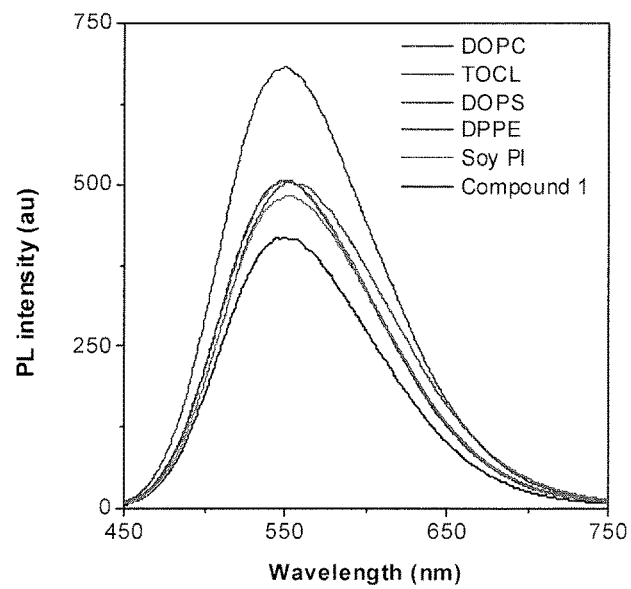
FIG. 11 shows emission spectra of Compound 1 in the presence of LUVs with different phospholipids.
Figure 12:
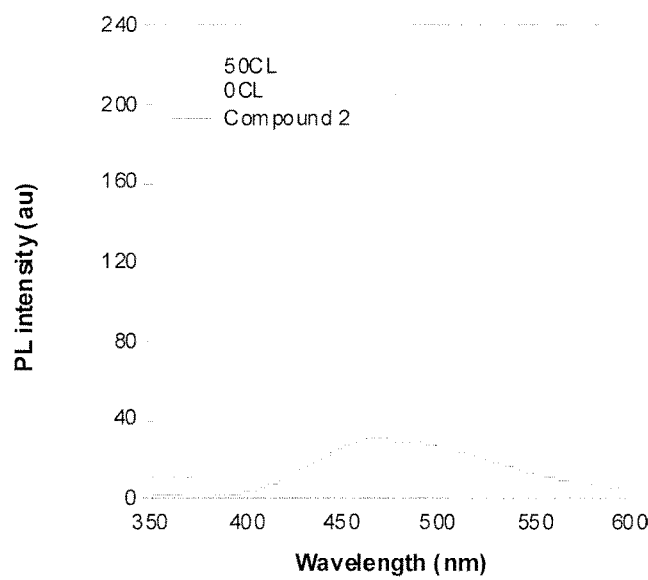
FIG. 12 shows emission spectra of Compound 2 with CL-containing and CL-free all-component vesicles.
Figure 13:
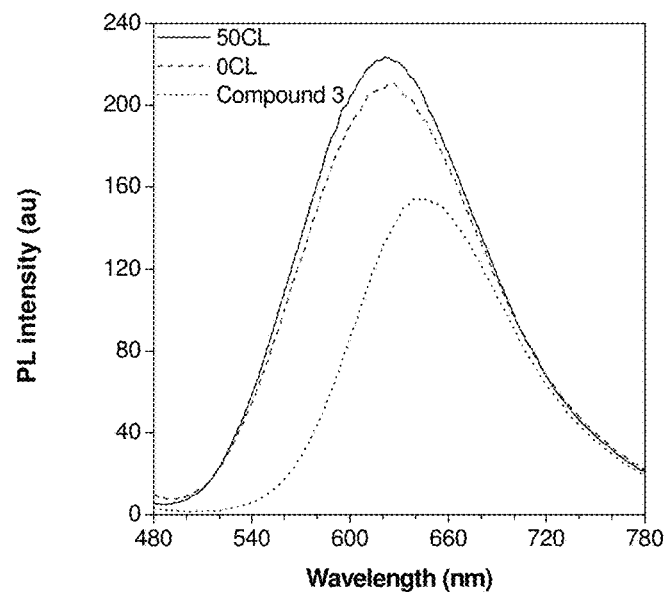
FIG. 13 shows emission spectra of Compound 3 with CL-containing and CL-free all-component vesicles.
Figure 14:
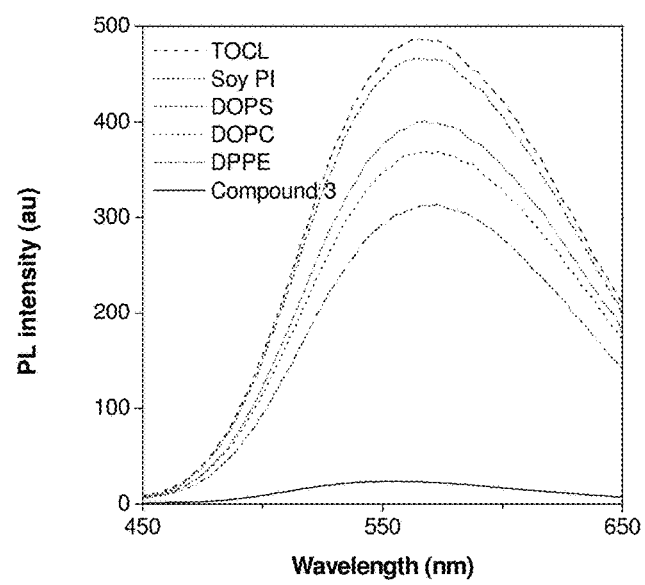
FIG. 14 shows emission spectra of Compound 3 in the presence of LUVs with different phospholipids.
Figure 15:
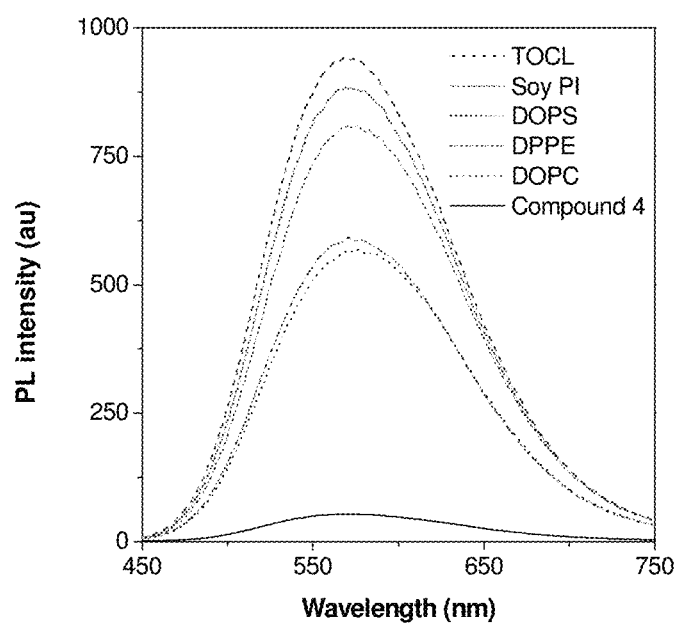
FIG. 15 shows emission spectra of Compound 4 in the presence of LUVs with different phospholipids.

In addition to CL detection, the utility of TTAPE-Me for mitochondria quantification was demonstrated. Individual mitochondria from *S. cerevisiae* strain YPH 500 have been isolated and calibrated by Biuret test. As shown in FIG. 10A, the emission of TTAPE-Me increases gradually with the increase of mitochondria amount. A linear relationship is well established between the fluorescence intensity of TTAPE-Me and mitochondria concentration. Isolated mitochondria can be clearly visualized under fluorescence microscope with TTAPE-Me as the stain (FIG. 10B-10C), results of which show that by using TTAPE-Me, quantification of mitochondria can be accomplished in a simple, easy manner with high sensitivity and low background noise. In contrast, time-consuming and intricate procedures are involved when using NAO for the quantification of isolated mitochondria. The isolated mitochondria are fixed by formaldehyde, followed by multiple rinsing, centrifugation and resuspension steps. Further, the signal-to-noise ratio by using NAO is much smaller, likely due to the strong background of NAO in solution.

In summary, a water-soluble AIE fluorogen, TTAPE-Me, has been developed for the detection and quantification of CL, a unique phospholipid in mitochondrial inner membrane. The fluorescence of TTAPE-Me is selectively turned on by CL-containing vesicles and the intensity is proportional to the concentration or fraction of CL. As a fluorescence turn-on sensor, TTAPE-Me can be used for quantitative analysis and visualization of isolated mitochondria. Compared with NAO, the only dye currently commercially available for CL sensing, TTAPE-Me provides much higher sensitivity and selectivity as well as a well-defined working mechanism without any difficult or ambiguous protocols. With all of these advantages, TTAPE-Me may be an ideal alternative of NAO for specific detection and quantification of CL, finding an array of applications in clinical diagnosis and mitochondria-related research.

Examples

Determination of CL Detection by TTAPE-Me

To determine whether TTAPE-Me can specifically detect CL, two types of large unilamellar vesicles (LUVs) 100-200 nm in diameter were prepared (FIG. 2A-2B). The CL-free vesicles were prepared by pure 1,2-dioleoyl-sn-glycero-4-phosphocholine (DOPC), which is the most abundant phospholipid in eukaryotic membranes. CL-containing vesicles were fabricated by the mixture of 1,1',2,2'-tetraoleoyl cardiolipin (TOCL) and DOPC, in which the zwitterionic DOPC is used to stabilize the vesicles. As shown in FIG. 1, the emission of TTAPE-Me is turned on in the presence of CL-containing vesicles.

General Synthesis of TTAPE-Me

Synthesis of 4,4'-bis(8-bromoethoxy)benzophenone (B)

1,8-dibromoethane (3.8 g, 14.0 mmol) was added to a mixture of 4,4'-dihydroxybenzophenone (1.0 g, 4.7 mmol) and potassium carbonate (1.3 g, 9.3 mmol) in acetone (50 mL). The mixture was refluxed under stirring for 12 h. After filtration and solvent evaporation, the crude product was purified by a silica gel column using chloroform as eluent. The product, B, was obtained as white powder in 66% yield (3.10 g). $R_f$=0.5 (chloroform). $^1$H NMR (400 MHz, CDCl3), δ (ppm): 7.78 (d, 4H), 6.94 (d, 4H), 4.05 (t, 4H), 3.42 (t, 4H), 1.89-1.80 (m, 8H), 1.48-1.39 (m, 16H). $^{13}$C NMR (100 MHz, CDCl3), δ (ppm): 193.9, 161.8, 131.6, 129.9, 113.3, 67.5, 33.3, 32.1, 28.5, 28.4, 28.0, 27.4, 25.3.

Synthesis of 1,1,2,2-tetrakis[4-(8-bromoethoxy)phenyl]-ethene (C)

In a suspension of B (1.0 g, 1.7 mmol) in 50 mL of THF were added TiCl4 (0.19 mL, 1.7 mmol) and Zn dust (0.22 g, 3.4 mmol). After refluxing for 20 hours, the reaction mixture was cooled to room temperature and filtered. The solvent was evaporated under vacuum and the crude product was purified by a silica gel column using a chloroform/hexane (1:1 v/v) mixture as eluent. The product, C, was obtained as yellow viscous liquid in 62% yield (0.6 g). $R_f$=0.5 (chloroform/hexane=1:1). $^1$H NMR (400 MHz, CDCl3), δ (ppm): 6.99-6.90 (m, 8H), 6.63-6.60 (m, 8H), 3.87-3.80 (m, 8H), 3.41-3.39 (m, 8H), 1.86-1.70 (m, 16H), 1.34-1.26 (m, 32H). $^{13}$C NMR (100 MHz, CDCl3), δ (ppm): 157.9, 137.5, 133.2, 129.9, 114.2, 68.3, 55.6, 34.7, 33.4, 29.9, 29.3, 28.7, 26.6.

Synthesis of 1,1,2,2-tetrakis[4-(2-trimethylammonio-ethoxy)phenyl]ethene Tetrabromide (TTAPE-Me)

Quaternization of C with an excess amount of trimethylamine generated TTAPE-Me. The product was obtained as pale yellow powder in 85% yield. $^1$H NMR (400 MHz, D2O), δ (ppm): 7.09 (d, 8H), 6.83 (d, 8H), 4.46 (t, 8H), 3.80 (t, 8H), 3.25 (s, 36H). $^{13}$C NMR (100 MHz, D2O), δ (ppm): 155.4, 139.2, 137.4, 132.3, 113.7, 64.8, 61.6, 53.7. MS (TOF), m/e 855.6561 ([M-2Br-3CH3]$^+$, calcd. 855.6725).

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

We claim:
1. A one-step method of detecting and quantifying cardiolipin in a sample using a positively charged aggregation induced emission (AIE) luminogen comprising:
   introducing the AIE luminogen to a solution containing the sample; and
   measuring fluorescence intensity of the solution, wherein the AIE luminogen binds to cardiolipin in vesicles and comprises a structure having a formula of

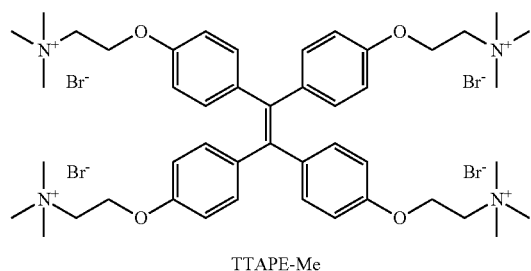

TTAPE-Me

2. The method of claim 1, wherein the AIE luminogen binds negatively charged cardiolipin solely by electrostatic interaction.

3. A method of quantifying isolated mitochondria using a positively charged AIE luminogen comprising:
   staining a sample containing isolated mitochondria with the AIE luminogen; and
   measuring the fluorescence intensity wherein the AIE luminogen comprises a structure having a formula of

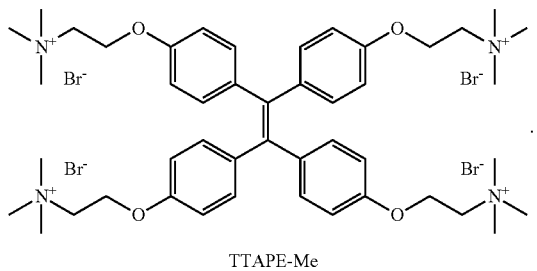

TTAPE-Me

4. The method of claim 3, wherein the quantified isolated mitochondria is from *Saccharomyces cerevisiae* strain YPH 500 of yeast.

5. A method of quantifying isolated mitochondria using a positively charged AIE luminogen comprising:
   introducing the AIE luminogen to a sample containing isolated mitochondria, wherein the AIE luminogen stains the isolated mitochondria; and
   identifying the stained isolated mitochondria under microscope wherein the AIE luminogen comprises a structure having a formula of

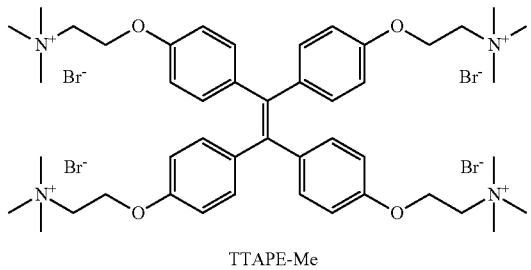

TTAPE-Me

6. The method of claim 5, wherein the quantified isolated mitochondria is from *Saccharomyces cerevisiae* strain YPH 500 of yeast.

\* \* \* \* \*